United States Patent
Pu

(10) Patent No.: US 8,193,520 B2
(45) Date of Patent: Jun. 5, 2012

(54) PARTICLE BEAM THERAPY SYSTEM

(75) Inventor: Yuehu Pu, Chiyoda-ku (JP)

(73) Assignee: Mitsubishi Electric Corporation, Tokyo (JP)

( * ) Notice: Subject to any disclaimer, the term of this patent is extended or adjusted under 35 U.S.C. 154(b) by 98 days.

(21) Appl. No.: 12/724,844

(22) Filed: Mar. 16, 2010

(65) Prior Publication Data

US 2010/0301228 A1     Dec. 2, 2010

(30) Foreign Application Priority Data

May 27, 2009    (JP)  ................................. 2009-127803

(51) Int. Cl.
*H01J 3/08*     (2006.01)
*G21K 1/10*     (2006.01)
(52) U.S. Cl. .................. 250/505.1; 250/492.3
(58) Field of Classification Search ............... 250/492.3, 250/505.1
See application file for complete search history.

(56) References Cited

U.S. PATENT DOCUMENTS

| | | | | |
|---|---|---|---|---|
| 5,039,867 A | * | 8/1991 | Nishihara et al. | 250/492.3 |
| 6,710,362 B2 | * | 3/2004 | Kraft et al. | 250/492.3 |
| 2006/0033042 A1 | * | 2/2006 | Groezinger et al. | 250/492.1 |
| 2007/0164227 A1 | * | 7/2007 | Yoshida | 250/396 ML |
| 2011/0105821 A1 | * | 5/2011 | Dieter et al. | 600/1 |

FOREIGN PATENT DOCUMENTS

| | | |
|---|---|---|
| JP | 10-199700 | 7/1998 |
| JP | 2006-341010 | 12/2006 |
| JP | 2008-161716 | 7/2008 |
| WO | WO 2009/026997 A1 | 3/2009 |

* cited by examiner

*Primary Examiner* — Jack Berman
*Assistant Examiner* — Eliza Osenbaugh-Stewart
(74) *Attorney, Agent, or Firm* — Oblon, Spivak, McClelland, Maier & Neustadt, L.L.P.

(57) ABSTRACT

There is provided a particle beam therapy system that can rapidly change beam energy without increasing the size of a deflection electromagnet even in the case where the number of required beam-energy changes is large.

There is provided a plurality of beam energy changing units each provided with a beam energy attenuation unit; a beam is deflected in such a way as to sequentially passes through the plurality of beam energy changing units; while a beam passes through one of the beam energy changing unit, the beam energy attenuation amount of another beam energy changing unit is changed.

8 Claims, 10 Drawing Sheets

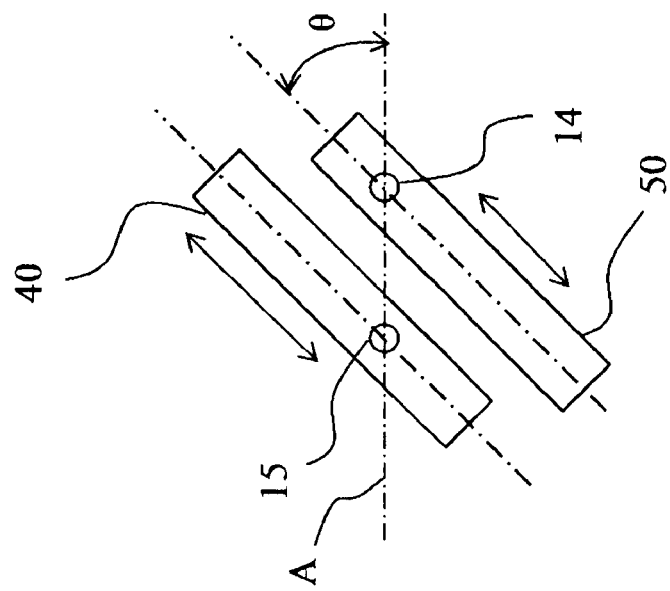
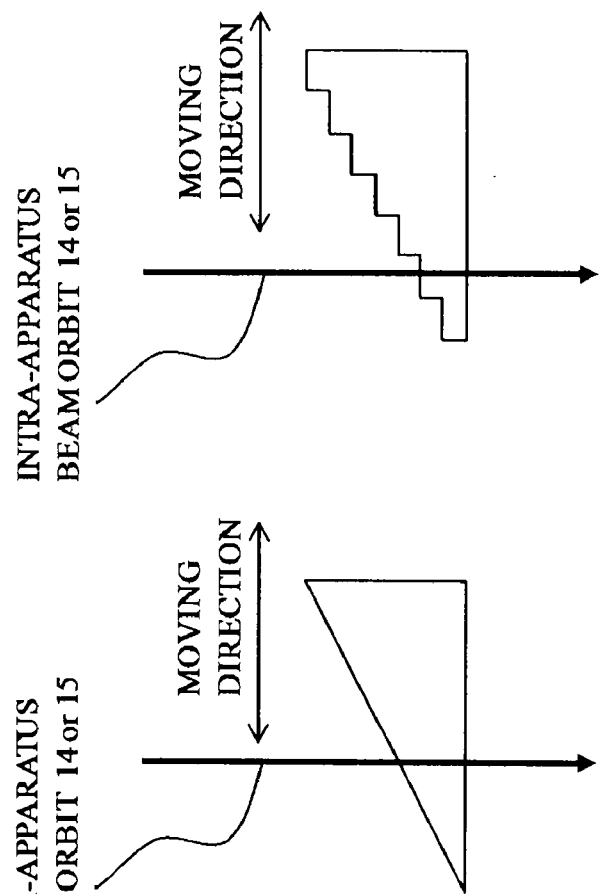
FIG. 6C
FIG. 6B
FIG. 6A

US 8,193,520 B2

PARTICLE BEAM THERAPY SYSTEM

BACKGROUND OF THE INVENTION

1. Field of the Invention

The present invention relates to a particle beam therapy system that performs therapy by irradiating a particle beam onto a diseased site such as a tumor, and particularly to a three-dimensional-irradiation particle beam therapy system that irradiates a particle beam in accordance with the three-dimensional shape of a diseased site.

2. Description of the Related Art

In a treatment method based on a particle beam, a high-energy particle beam, such as a proton beam or a carbon beam accelerated up to 70% of the light velocity, is utilized. These high-energy particle beams have the following features when irradiated into a body. Firstly, almost all of irradiated particle beams stop at a position of a depth proportional to the particle beam energy raised to the $1.7^{th}$ power. Secondly, the density (referred to as a dose) of energy, which is given to the path through which an irradiated particle beam passes until it stops in a body, becomes maximum at a position where the particle beam stops. A distinctive deep dose distribution curve formed along a path through which a particle beam passes is referred to as a Bragg curve. The position where the dose value becomes maximum is referred to as a Bragg peak.

A particle beam three-dimensional irradiation apparatus is contrived in such a way that, while it scans the Bragg peak position in accordance with the three-dimensional shape of a tumor and adjusts the peak dose at each scanning position, a predetermined three-dimensional dose distribution is formed in a tumor region, which is a target preliminarily determined by an imaging diagnosis. The scanning of the position where a particle beam stops includes scanning in transverse directions (X and Y directions) that are approximately perpendicular to the irradiation direction of a particle beam and scanning in a depth direction (Z direction) that is the irradiation direction of a particle beam. In the transverse-direction scanning, there exists a method of moving the position of a patient with respect to a particle beam and a method of moving the position of a particle beam by use of an electromagnet or the like; in general, the method utilizing an electromagnet is adopted. The method of scanning in the depth direction is performed only by changing the energy of a particle beam. As the method of changing energy, there exists a method of changing the energy of a particle beam by means of an accelerator and a method of inserting an energy attenuator into a path through which a particle beam passes and changing the attenuation amount of the attenuator. Such a method of changing the energy of a beam by varying the attenuation amount of an attenuator is disclosed, for example, in Patent Document 1 (Japanese Patent Application Laid-Open No. 2006-341010) or Patent Document 2 (Japanese Patent Application Laid-Open No. H10-199700).

The number of beam-energy changes in an actual particle beam therapy system depends on the size of a target, the king of a particle beam, and the maximum energy; as may be necessary, the beam energy is required to be changed approximately 100 times during irradiation. Accordingly, the speedup of beam-energy change leads to the reduction of a therapy time and the enhancement of the accuracy. In FIG. 2 of Patent Document 1, there is disclosed a beam energy changing apparatus that rapidly changes the energy of a beam. In this conventional technology, a beam that enters the beam energy changing apparatus is once deflected from the incident direction by use of two pairs, i.e., totally four deflection electromagnets; the particle beam that has reached a certain position is bent again to the opposite direction; the traveling direction of the particle beam is made to coincide with an orbit that is approximately in parallel with the extended line of the incident direction of the incident beam. The particle beam that has traveled a predetermined distance along the parallel orbit is bent in such a way as to return to the extended line of the incident direction of the particle beam. A range shifter (energy attenuator) having portions of different thicknesses is disposed in the parallel orbits; by changing parameters for the four electromagnets, the parallel orbits are made to correspond to the portions of different thicknesses of the range shifter so that the energy of an incident particle beam is changed. The particle beam, the energy of which has been changed, is transported to the particle beam irradiation apparatus.

According to the methods disclosed in FIG. 2 of Patent Document 1, the energy of a particle beam can extremely rapidly be changed compared with the method, disclosed in FIG. 6 of Patent Document 2, in which a range shifter is mechanically moved. However, in the case where the number of required beam-energy changes is large, the size of the range shifter becomes large and hence it is required to deflect a particle beam by a large angle; therefore, the size of the electromagnet becomes large.

SUMMARY OF THE INVENTION

The objective of the present invention is to provide a particle beam therapy system that can rapidly change beam energy without increasing the size of the deflection electromagnet even in the case where the number of required beam-energy changes is large.

In order to solve the foregoing problems, the present invention utilizes the following configuration. That is to say, a particle beam therapy system according to the present invention includes a beam energy changing unit that changes the energy of an incident particle beam; a beam energy change control unit that outputs a command for controlling the beam energy changing unit; an irradiation unit that irradiates a particle beam exiting from the beam energy changing unit onto an irradiation subject; and an irradiation control unit that outputs a command for controlling the energy and position of a particle beam to be irradiated onto the irradiation subject. The beam energy changing unit includes deflection electromagnets that sequentially deflect the incident particle beam into a plurality of intra-apparatus beam orbits, variable energy attenuation units disposed in the respective intra-apparatus beam orbits, and a deflection electromagnet that performs deflection in such a way that particle beams that pass through the respective variable energy attenuation units fall into a single and the same orbit; and while a particle beam passes through one of the variable energy attenuation units, the beam energy change control unit performs control in such a way as to change the energy attenuation amount of at least one of the other variable energy attenuation units, based on the command from the irradiation control unit.

In the particle beam therapy system according to the present invention, not only energy changing can rapidly be performed even in the case where the number of required beam energy changes (the number of required beam energy levels) is large, but also it is not required to increase the deflection amount of a deflection electromagnet for changing beam energy. Therefore, there can be achieved the downsizing and cost reduction of a beam energy changing unit and a particle beam therapy system provided with the beam energy changing unit.

The foregoing and other object, features, aspects, and advantages of the present invention will become more apparent from the following detailed description of the present invention when taken in conjunction with the accompanying drawings.

BRIEF DESCRIPTION OF THE DRAWINGS

FIG. 6 is a diagram illustrating a variable energy attenuator according to Embodiment 3 of the present invention;

DETAILED DESCRIPTION OF THE PREFERRED EMBODIMENTS

Embodiment 1

Figure 1:
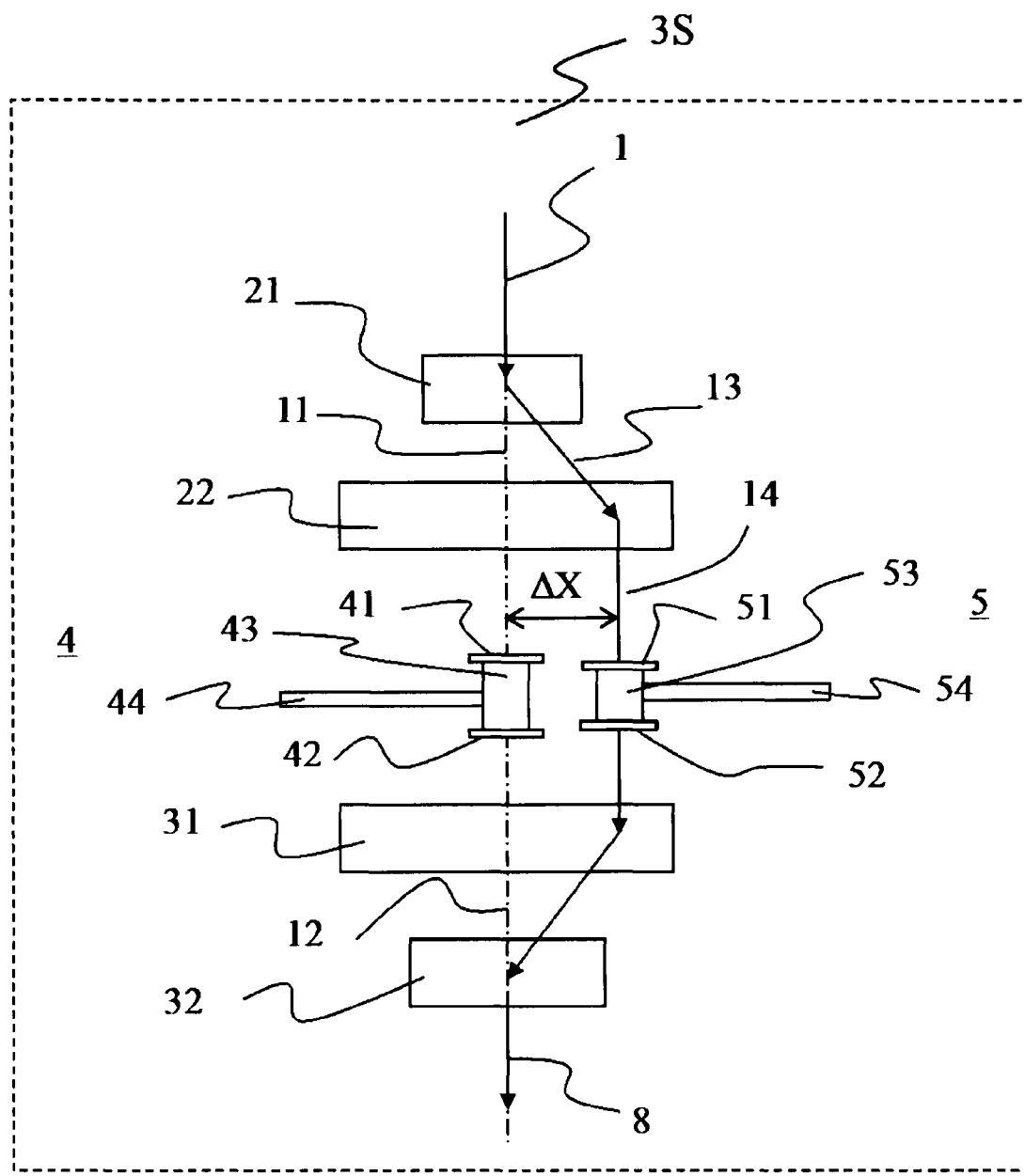
FIG. 1 is a schematic block diagram illustrating a beam energy changing unit according to Embodiment 1 of the present invention.

The configuration and the operation of a particle beam therapy system according to Embodiment 1 of the present invention will be explained with reference to FIGS. 1, 2, and 3. FIG. 2 is a block diagram illustrating the system outline of a particle beam therapy system that is common to each embodiment of the present invention. In FIG. 2, reference character 1S denotes a particle beam accelerator that accelerates a particle beam to a level at which the particle beam has predetermined energy; 2S denotes a particle beam transport unit, formed of an electromagnet and the like, that transports a particle beam; 3S denotes a beam energy changing unit that is disposed after the particle beam accelerator; 4S denotes a beam energy change control unit that outputs a command for controlling the beam energy changing unit. Reference character 5S denotes an irradiation unit that irradiates a particle beam onto an irradiation subject (diseased site); the irradiation unit includes a scanning magnet, a beam monitor (unillustrated), and the like. Reference character 6S denotes an irradiation control unit that controls the irradiation unit 5S in accordance with an instruction from a treatment planning apparatus (unillustrated) and outputs a command to the beam energy change control unit so as to control a particle beam to be irradiated onto a diseased site. Reference numeral 1 denotes an incident particle beam that enters the beam energy changing unit 3S; reference numeral 8 denotes a particle beam that exits from the beam energy changing unit 3S after the energy thereof is changed. In addition, in FIG. 2, the particle beam transport unit 2S, the beam energy changing unit 3S, and the irradiation unit 5S are expressed with respective blocks; however, there may be a case where each constituent unit completely or partially includes another constituent unit, for example, the foregoing units have a common electromagnet.

Figure 2:
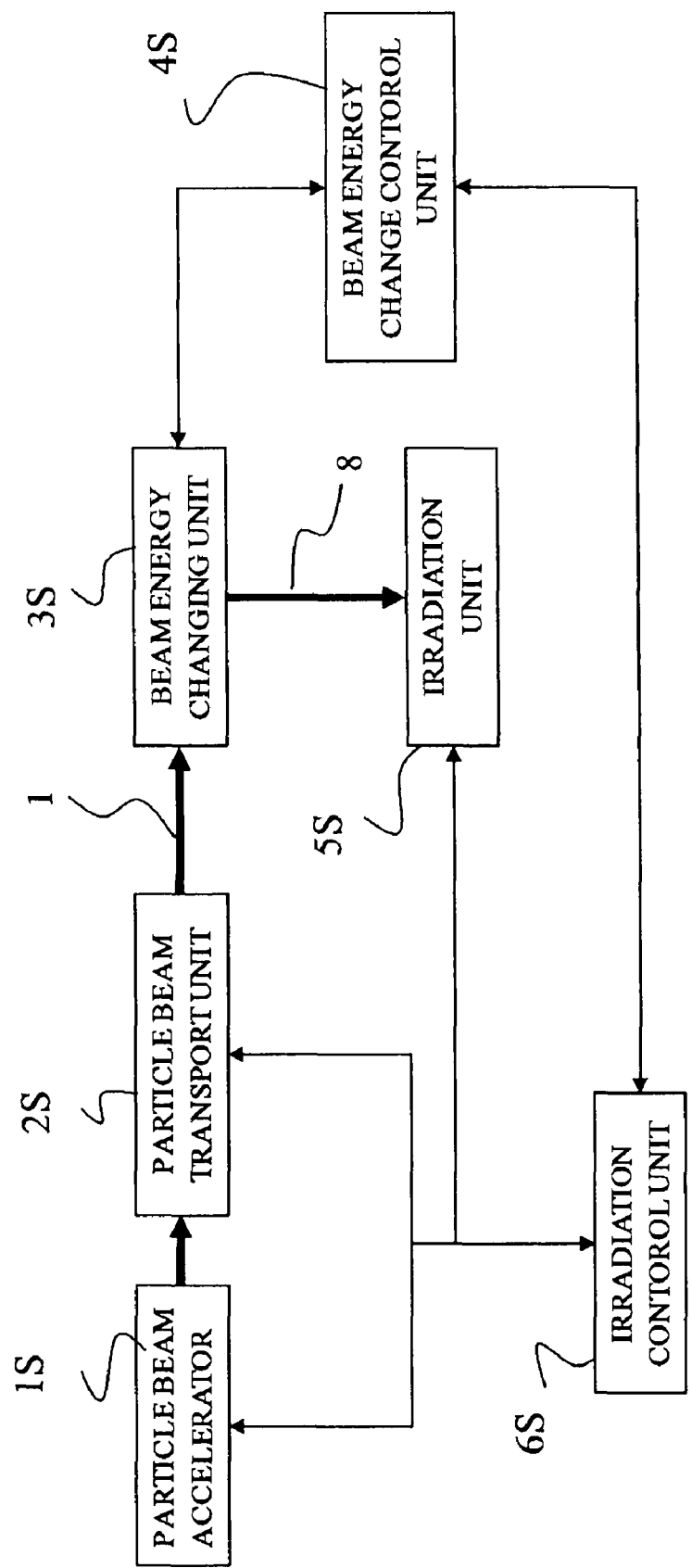
FIG. 2 is a block diagram illustrating the system outline of a particle beam therapy system that is common to each embodiment of the present invention.

FIG. 1 is a diagram illustrating the schematic configuration of a beam energy changing unit 3S according to Embodiment 1 of the present invention. In FIG. 1, as is the case with FIG. 2, reference numeral 1 denotes an incident particle beam (hereinafter, there may be a case where a "particle beam" is abbreviated to a "beam"); reference numeral 8 denotes a particle beam whose energy has been changed. Reference numeral 21 denotes a first deflection electromagnet in the energy changing unit; reference numeral 22 denotes a second deflection electromagnet; reference numeral 31 denotes a third deflection electromagnet; reference numeral 32 denotes a fourth deflection electromagnet. Reference numerals 11 and 12 denote the extended line of the incident particle beam 1 or a particle beam orbit along the extended line. Reference numeral 13 denotes the orbit of a particle beam bent by the first electromagnet 21. Reference numeral 4 denotes a first variable energy attenuation unit formed of a shape-variable container; reference numeral 5 denotes a second variable energy attenuation unit formed of a shape-variable container. Reference numeral 41 denotes the beam incident face of the shape-variable container; reference numeral 42 denotes the beam exit face. Reference numeral 43 denotes the shape-variable container; the side faces thereof are formed of a material, such as a bellows, that can change its shape. Reference numeral 44 denotes a tube connected with the shape-variable container 43; through the tube 44, a fluid, such as water, for attenuating (absorbing) particle beam energy is introduced into or drained from the shape-variable container 43. For example, by changing the quantity or the pressure of water with which the shape-variable container 43 is filled, the side face of the shape-variable container 43 formed of a bellows is deformed, so that the thickness of the water contained between the beam incident face 41 and the beam exit face 42 changes. Similarly, reference numerals 51 and 52 denote the beam incident face and the beam exit face, respectively, of a second variable energy attenuation unit 5. Reference numeral 54 denotes a tube for introducing a fluid such as water into the shape-variable container 53 or draining the fluid from the shape-variable container 53. The second variable energy attenuation unit 5 operates in the same manner as the first variable energy attenuation unit 4 does.

In FIG. 1, reference numeral 14 denotes the orbit (hereinafter, referred to as an intra-energy-changing-unit beam orbit or an intra-apparatus beam orbit) of a particle beam that passes through the second variable energy attenuation unit 5. In some cases, reference numerals 11 and 12 are referred to as first intra-apparatus beam orbits, and reference numeral 14 is referred to as a second intra-apparatus beam orbit. $\Delta X$ denotes the distance between the first intra-apparatus beam orbit 12 and the second intra-apparatus beam orbit 14. The distance $\Delta X$ is determined in such a way that the first variable energy attenuation unit 4 and the second variable energy attenuation unit 5 can be arranged without interfering with each other. The distance $\Delta X$ depends on the respective dimension, in the direction perpendicular to the beam orbit, of the first variable energy attenuation unit 4 and the respective dimension, in the direction perpendicular to the beam orbit, of the second variable energy attenuation unit 5. It is required to increase the distance $\Delta X$ in proportion to the sizes of the first variable energy attenuation unit 4 and the second variable energy attenuation unit 5. It is required to make the cross-sectional sizes of the portions, through which a beam passes, of the first variable energy attenuation unit 4 and the second variable energy attenuation unit 5 slightly larger than the size of a beam that has passed through the first variable energy attenuation unit 4 or the second variable energy attenuation unit 5.

Figure 3:
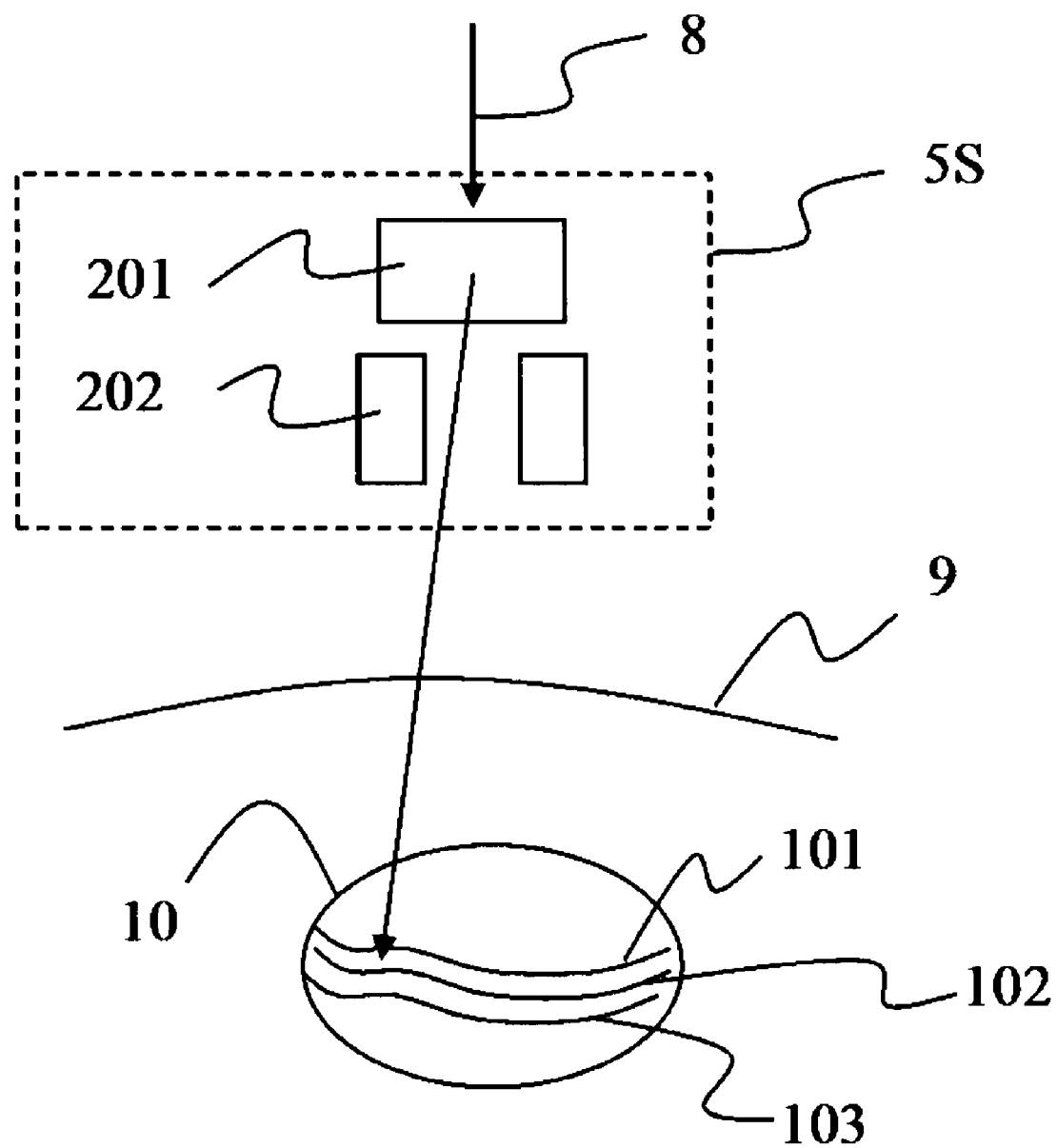
FIG. 3 is a conceptual diagram illustrating an irradiation unit of a particle beam therapy system that is common to each embodiment of the present invention.

FIG. 3 is a conceptual diagram illustrating the irradiation unit 5S of the particle beam therapy system and an irradiation subject. In FIG. 3, reference numeral 8 denotes a particle beam whose energy has been changed; reference numerals 201 and 202 denote scanning mechanisms that scan the particle beam 8 whose energy has been changed so as to irradiate it onto a diseased site. The scanning mechanisms are formed of a deflection electromagnet, for example. Reference numeral 9 denotes the body surface of a patient; reference numeral 10 denotes a target region (tumor, diseased site), which is an irradiation subject. Each of reference numerals 101, 102, and 103 indicates an example of diseased-site slice corresponding to the amount of beam energy. In other words, the energy of a beam irradiated onto the slice 103 is slightly larger than the energy of a beam irradiated onto the slice 102. By changing the energy of a beam, the Bragg peak position of a particle beam is moved into each depth region of the diseased site 10, and by utilizing the scanning magnets 201 and 202, the particle beam is scanned transversely, so that three-dimensional irradiation can be performed.

Next, the operation of a particle beam therapy system according to Embodiment 1 of the present invention will be explained. At first, by means of a treatment planning apparatus (unillustrated), there is determined the maximum beam energy E0 required to perform irradiation onto the diseased site 10. Simultaneously, there is determined beam energy Ei (i=1, 2, 3, - - - n) required to perform irradiation onto each of the different-depth positions of the diseased site 10, as indicated by reference numerals 101 through 103 illustrated in FIG. 3. There is determined a transverse position (Xi, Yi) for performing irradiation onto the respective positions of the diseased site 10. Furthermore, there is preliminarily determined an irradiation dose value for each position. Planning information including the foregoing items is transmitted to the irradiation control unit 6S.

In this situation, at first, corresponding to beam energy E1 required for a position onto which irradiation is to be performed, the beam energy change control unit 4S performs setting of parameters for the beam energy changing unit 3S, in accordance with a command from the irradiation control unit 6S. Specifically, the beam energy change control unit 4S sets the respective excitation current values of the first deflection electromagnet 21, the second deflection electromagnet 22, the third deflection electromagnet 31, and the fourth deflection electromagnet 32 in the beam energy changing unit 3S to the values, corresponding to the first intra-apparatus beam orbits 11 and 12 (or the second intra-apparatus beam orbits 13 and 14), which have been preliminarily determined. In the example illustrated in FIG. 1, setting corresponding to the first intra-apparatus beam orbits 11 and 12 is setting that does not deflect a beam; therefore, the excitation currents of all deflection electromagnets become zero. Simultaneously, the thickness of the first variable energy attenuation unit 4 is set to T1. T1 is a value corresponding to a necessary energy attenuation amount (E0-E1). Here, E0 is the energy of an incident particle beam that enters the beam energy changing unit.

The setting of the thickness of the first variable energy attenuation unit 4 can specifically be realized, for example, by, through the tube 44, adjusting the pressure of the water with which the shape-variable container 43 is filled and changing the distance between the face 41 and the face 42. Then, after the setting of the thickness T1 of the first variable energy attenuation unit 4 and the setting of all the deflection electromagnets are completed, the beam energy change control unit 4S transmits a setting completion signal to the irradiation control unit 6S. Simultaneously, the irradiation control unit 6S controls all other apparatuses, such as electromagnets, including the irradiation unit 5S in such a way that they correspond to the energy E1.

In response to a command from the irradiation control unit 6S, the particle beam accelerator 1S accelerates a particle beam so that it has as much energy as the required maximum energy E0. The particle beam is transported by the particle beam transport unit 2S to a predetermined downstream apparatus. Then, the incident particle beam 1 whose beam energy is E0 enters the beam energy changing unit 3S.

Because, in the foregoing setting, setting is performed in such a way that the incident particle beam 1 passes through the first intra-apparatus beam orbits 11 and 12, the incident particle beam 1 advances straight without being deflected and passes through the first variable energy attenuation unit 4; then, the beam energy of the particle beam 8 whose energy has been changed becomes E1. After that, the energy-changed particle beam 8 having beam energy E1 enters the irradiation unit 5S. The energy-changed particle beam 8 is irradiated onto the planned position (X1, Y1) by means of the scanning electromagnets 201 and 202; the depth position Z1 thereof corresponds to the beam energy E1. Normally, in a treatment plan, the order of irradiation can be determined in such a way that irradiation is collectively performed onto irradiation positions where the same beam energy is required. Accordingly, assuming that the slice 103 is a slice corresponding to, for example, E1, a beam having beam energy E1 can be irradiated onto all planned irradiation positions within the slice 103 by use of the scanning magnets 201 and 202. The irradiation time for a single slice depends on the beam current intensity, the prescription dose to be irradiated onto the whole tumor, and the depth of the slice; it is approximately several hundred milliseconds.

Immediately after the incident particle beam 1 is introduced into the first intra-apparatus beam orbits 11 and 12 so as to pass through the first variable energy attenuation unit 4 and then irradiation onto the slice 103 corresponding to E1 is started, the irradiation control unit 6S outputs a command to the beam energy change control unit 4S so as to control the second variable energy attenuation unit 5 so that the energy attenuation amount corresponds to beam energy E2 in the slice 102 onto which irradiation is performed next. Then, when, after the irradiation onto the slice 103 corresponding to E1 ends, confirming that the setting (setting of all apparatuses, which require setting, including the energy changing unit 3S and the irradiation unit 5S) corresponding to the beam energy E2 has been completed, the irradiation control unit 6S immediately excites, through the beam energy change control unit 4S, the deflection electromagnets 21, 22, 31, and 32 up to the values determined so that a particle beam passes through the second intra-apparatus beam orbits 13 and 14; then, the incident particle beam 1 is introduced into the second intra-apparatus beam orbit. The particle beam passes through the second variable energy attenuation unit 5 that has been set so as to have a thickness T2 corresponding to the beam energy E1, i.e., so that the energy attenuation amount becomes (E0-E2); then, the particle beam becomes the energy-changed particle beam 8 having the beam energy E2. After that, the energy-changed particle beam 8 is irradiated onto a diseased site region in the slice 102 corresponding to E2, by means of the particle-beam scanning magnets 201 and 202.

In this situation, in the foregoing operation, at the same time when the excitation of the deflection electromagnets 21, 22, 31, and 32 ends, a thickness T3, which corresponds to beam energy E3 in the slice 101 onto which the next irradiation is to be performed, is again set in the first variable energy attenuation unit 4. In general, the time required to change the thickness (hereinafter, referred to as a thickness-changing time) is proportional to the difference between the post-change thickness T3 and the pre-change thickness T2; however, because this change is performed during irradiation onto the slice 102, the total irradiation time can be less affected by the thickness-changing time. For example, in the case where the thickness-changing time is shorter than the irradiation time for the slice 102, the total irradiation time is not affected at all by the thickness-changing time. The switching time for switching the excitation state of the deflection electromagnets 21, 22, 31, and 32 from "zero excitation" to "excitation" is proportional to the inter-orbit distance $\Delta X$ indicated in FIG. 1; in the case where $\Delta X$ is 20 mm, the switching time is the same as or shorter than 10 msec even with a just normal electromagnet. That is to say, by utilizing a system according to the present invention, beam energy can rapidly be changed in the order of milliseconds.

Immediately after the irradiation onto the slice 102 ends, the completion of changing the thickness of the first variable energy attenuation unit is confirmed, and then the excitation of the deflection electromagnets 21, 22, 31, and 32 is switched to zero, so that irradiation onto the next slice 101 corresponding to the beam energy E3 can be started.

As described above, by alternatively introducing the incident particle beam 1 into the first variable energy attenuation unit 4 and the second variable energy attenuation unit 5, the respective energy attenuation amounts of the first variable energy attenuation unit 4 and the second variable energy attenuation unit 5 are alternatively changed to the attenuation amount corresponding to the next beam energy, so that there can rapidly be realized the irradiation corresponding to the required beam energy E1, E2, - - -, En.

According to the present invention, by alternatively utilizing two variable energy attenuation units, and by switching the two variable energy attenuation units for a particle beam through excitation and non-excitation of four electromagnets, beam energy change of several hundreds of stages can also be performed rapidly. The changing operation for the respective energy attenuation amounts of the variable energy attenuation units may be completed in a time that is shorter than a time required to perform irradiation onto a single slice; therefore, the noise and the mechanical vibration at a time when the thickness is changed in order to vary the energy attenuation amount can be reduced to an extent such that they are negligible.

According to the present invention, even in the case where the number of slices to be irradiated is large, the required beam deflection amount $\Delta X$ may be left small. In the present invention, assuming that the size of the beam 1 is 5 mm, the required deflection amount $\Delta X$ of the deflection electromagnet is determined by the cross-sectional sizes (each required to be more than 5 mm) of the two variable energy attenuation units 4 and 5; thus, $\Delta X$ can be set to 20 mm with a margin. In contrast, according to FIG. 2 of Patent Document 1, the required deflection amount of the deflection electromagnets 21, 22, 31, and 32 becomes n×$\Delta X$ when the number of slices is n. For example, in the case where n=10, the required deflection amount becomes approximately 200 mm. The deflection amount of 200 mm leads to the fact that not only large deflection electromagnets are required, but also the capacities of the power sources for the electromagnets also become large. In particular, in the case of a relatively heavy particle beam such as a carbon beam, the effect of the present invention is more remarkably demonstrated.

The present invention has an effect that, even in the case where the number of required beam energy changes is large, energy change can rapidly be performed, and the downsizing and the cost reduction of the beam energy changing unit can be realized without increasing the deflection amount of the deflection electromagnet.

Embodiment 2

Figure 4:
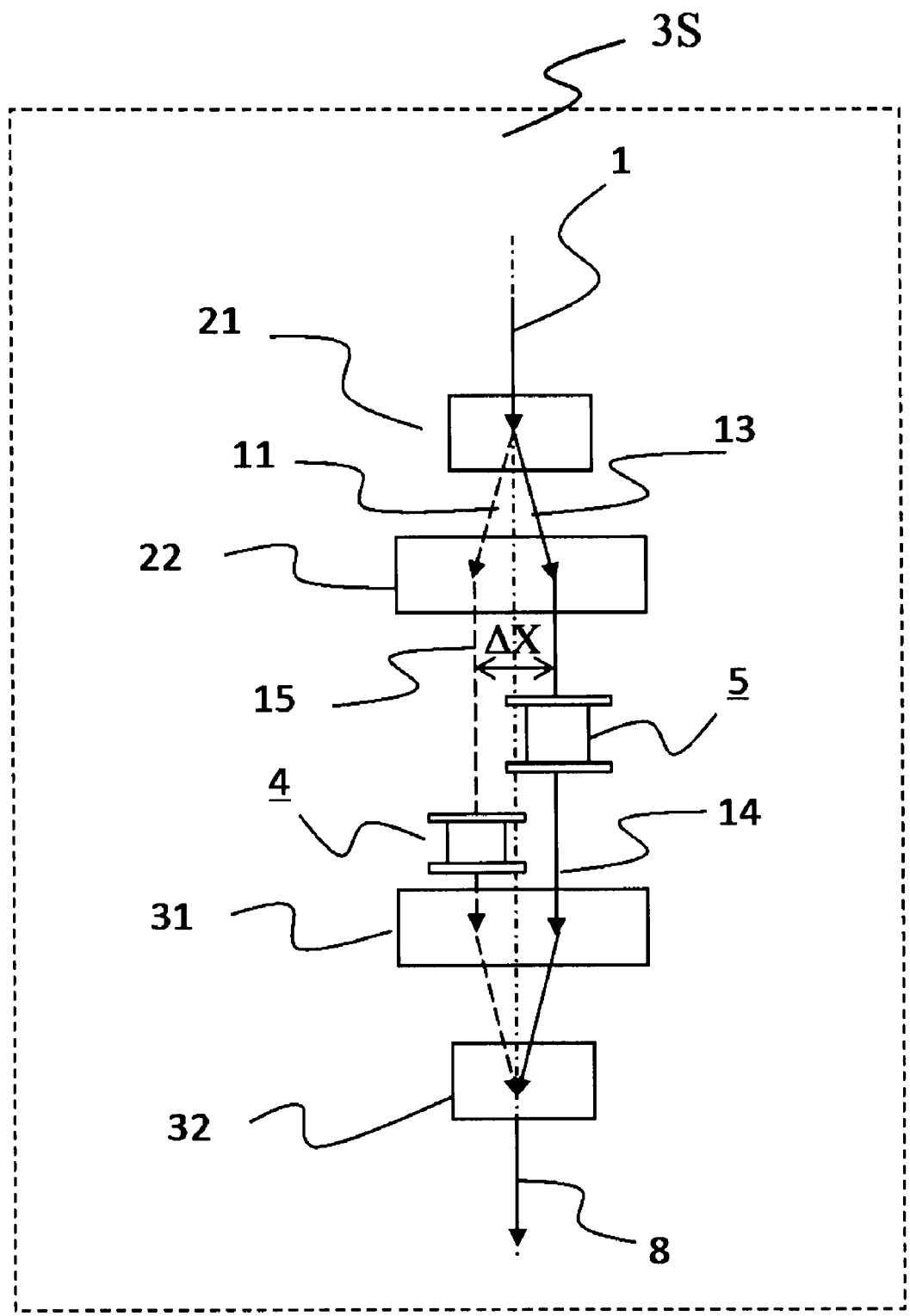
FIG. 4 is a schematic block diagram illustrating a beam energy changing unit according to Embodiment 2 of the present invention.

FIG. 4 is a configuration diagram of the beam energy changing unit 3S according to Embodiment 2 of the present invention. In Embodiment 1, there has been explained a case where the first intra-apparatus beam orbit is formed when all the excitation amounts for the first, the second, the third, and the fourth deflection electromagnets are zero; however, as illustrated in FIG. 4, the first intra-apparatus beam orbit may be formed by deflecting first intra-apparatus beam orbits 11 and 15 also, i.e., by deflecting them in a direction opposite to the directions of the second intra-apparatus beam orbits 13 and 14. When, in such a way as described above, the first intra-apparatus beam orbit and the second intra-apparatus beam orbit are formed in such a way as to be deflected in directions that are opposite to each other, the excitation currents for the deflection electromagnets 21, 22, 31, and 32 each become further smaller than the excitation current in FIG. 1, whereby the size of the deflection electromagnet is reduced.

In addition, the first variable energy attenuation unit 4 and the second variable energy attenuation unit 5 are arranged in the respective positions that are shifted from each other in the traveling direction of a beam in the intra-apparatus beam orbit. That is to say, the first variable energy attenuation unit 4 and the second variable energy attenuation unit 5 are arranged in such a way as to be perpendicular to the plane including the first intra-apparatus beam orbit 15 and the second intra-apparatus beam orbit 14 and in such a way that the projection image of the first variable energy attenuation unit 4, projected to a plane including the first intra-apparatus beam orbit 15 that passes through the first variable energy attenuation unit 4, and the projection image of the second variable energy attenuation unit 5, projected to a plane including the second intra-apparatus beam orbit 14 that passes through the second variable energy attenuation unit 5, do not overlap with each other. By, as described above, arranging the first variable energy attenuation unit 4 and the second variable energy attenuation unit 5 in such a way that they are shifted from each other, the distance $\Delta X$ between the first intra-apparatus beam orbit 15 and the second intra-apparatus beam orbit 14 can further be reduced compared with the beam energy changing unit illustrated in FIG. 1; therefore, the deflection electromagnets 21, 22, 31, and 32 can further be downsized.

It goes without saying that the configuration where two variable energy attenuation units are arranged in such a way as to be shifted from each other can be applied not only to Embodiment 2 but also to other embodiments of the present invention.

Embodiment 3

Figure 5:
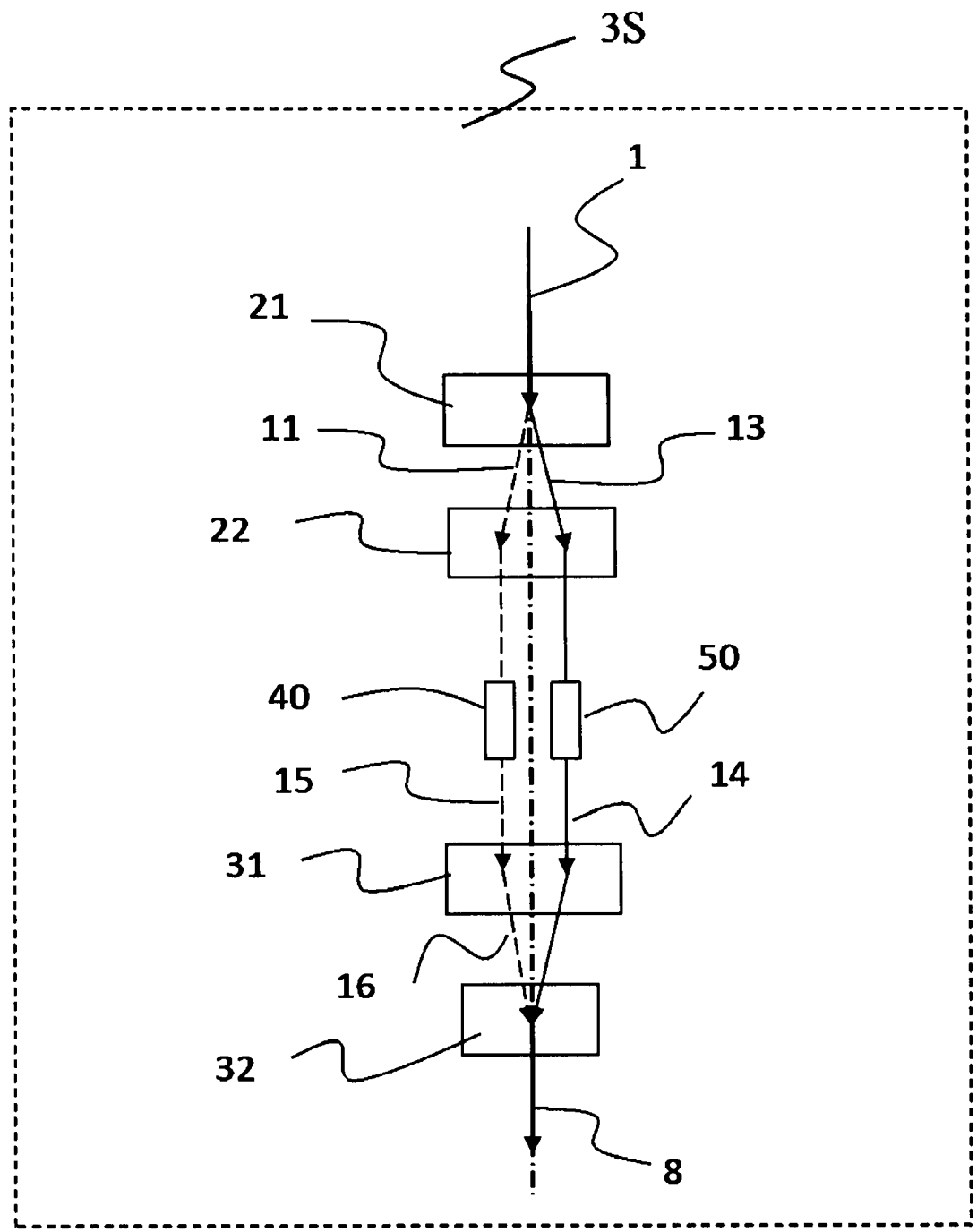
FIG. 5 is a schematic block diagram illustrating a beam energy changing unit according to Embodiment 3 of the present invention.

In Embodiments 1 and 2, there has been explained an example of variable energy attenuation unit where a shape-variable container is filled with water and the quantity of the contained water is adjusted and controlled so that the thickness of the water is changed; however, the present invention is not limited thereto; a variable energy attenuator of another configuration may be utilized in the variable energy attenuation unit. FIGS. 5 and 6 illustrate an embodiment showing this example. In FIG. 5, reference numeral denotes a first variable energy attenuation unit, and reference numeral 50 denotes a second variable energy attenuation unit; FIGS. 6A and 6B are a set of diagrams of particle beam energy attenuators of the variable energy attenuation units in FIG. 5, as viewed from side, i.e., a set of side views. The variable energy attenuation units 40 and 50 have a particle beam energy attenuator having a shape whose thickness changes in a wedge form, as illustrated in FIG. 6A, or in a stepped form, as illustrated in FIG. 6B, and a driving mechanism for moving the particle beam energy attenuator. The direction in which the particle beam energy attenuator is moved is a direction in which the thickness of the particle beam energy attenuator changes. In FIG. 5, the variable energy attenuation units 40 and 50 are installed in such a way that the direction in which the thickness changes is perpendicular to the plane of the paper of FIG. 5, i.e., the plane that includes the first intra-apparatus beam orbit 15 and the second intra-apparatus beam orbit 14.

FIG. 6C is a diagram for explaining further another installation direction for the particle beam energy attenuator.

FIG. 6C is a diagram of the variable energy attenuation units, as viewed from the top side of FIG. 5, i.e., as viewed in the traveling direction of a beam; FIG. 6C illustrates the positional relationship among the first intra-apparatus beam orbit 15, the second intra-apparatus beam orbit 14, the first variable energy attenuation unit 40, and the second variable energy attenuation unit 50. The particle beam energy attenuator may be provided at a predetermined angle θ from the plane A that includes the first intra-apparatus beam orbit 15 and the second intra-apparatus beam orbit 14. As described above, the direction in which the energy attenuator is provided may not necessarily be perpendicular to the plane A that includes the first intra-apparatus beam orbit 15 and the second intra-apparatus beam orbit 14; it is only necessary to provide the particle beam energy attenuator of the first variable energy attenuation unit 40 and the particle beam energy attenuator of the second variable energy attenuation unit 50 in a direction in which they do not interfere with each other.

Although, in Embodiments 1, 2, and 3, there has been described an example where the variable energy attenuation units are provided between the second deflection electromagnet and the third deflection electromagnet 31, the present invention is not limited thereto; the foregoing effect can be obtained wherever the variable energy attenuation units are provided, as long as they are provided between the first deflection electromagnet 21 and the fourth deflection electromagnet 32. However, when, as illustrated in FIGS. 1, 4, and 5, the variable energy attenuation units are provided between the second deflection electromagnet and the third deflection electromagnet, there can be demonstrated an effect that the overall configuration of the system can more simply be realized.

In Embodiments 1, 2, and 3, the first intra-apparatus beam orbit and the second intra-apparatus beam orbit have portions thereof that are approximately in parallel with each other, as illustrated in FIGS. 1, 4, and 5. However, the present invention is not limited thereto; as explained in Embodiment 5, described later, two or more intra-apparatus beam orbits may not necessarily have parallel portions, as long as the respective variable energy attenuation units provided in the intra-apparatus beam orbits are spaced apart from one another by distances with which they do not interfere with one another. In this regard, however, in the case where two or more intra-apparatus beam orbits have portions that are approximately in parallel with one another, by providing variable energy attenuation units in the respective portions, two or more variable energy attenuation units can be provided in parallel with one another; therefore, there is demonstrated an effect that the variable energy attenuation units are readily provided, and maintenance and repair can easily be performed.

Embodiment 4

Figure 7:
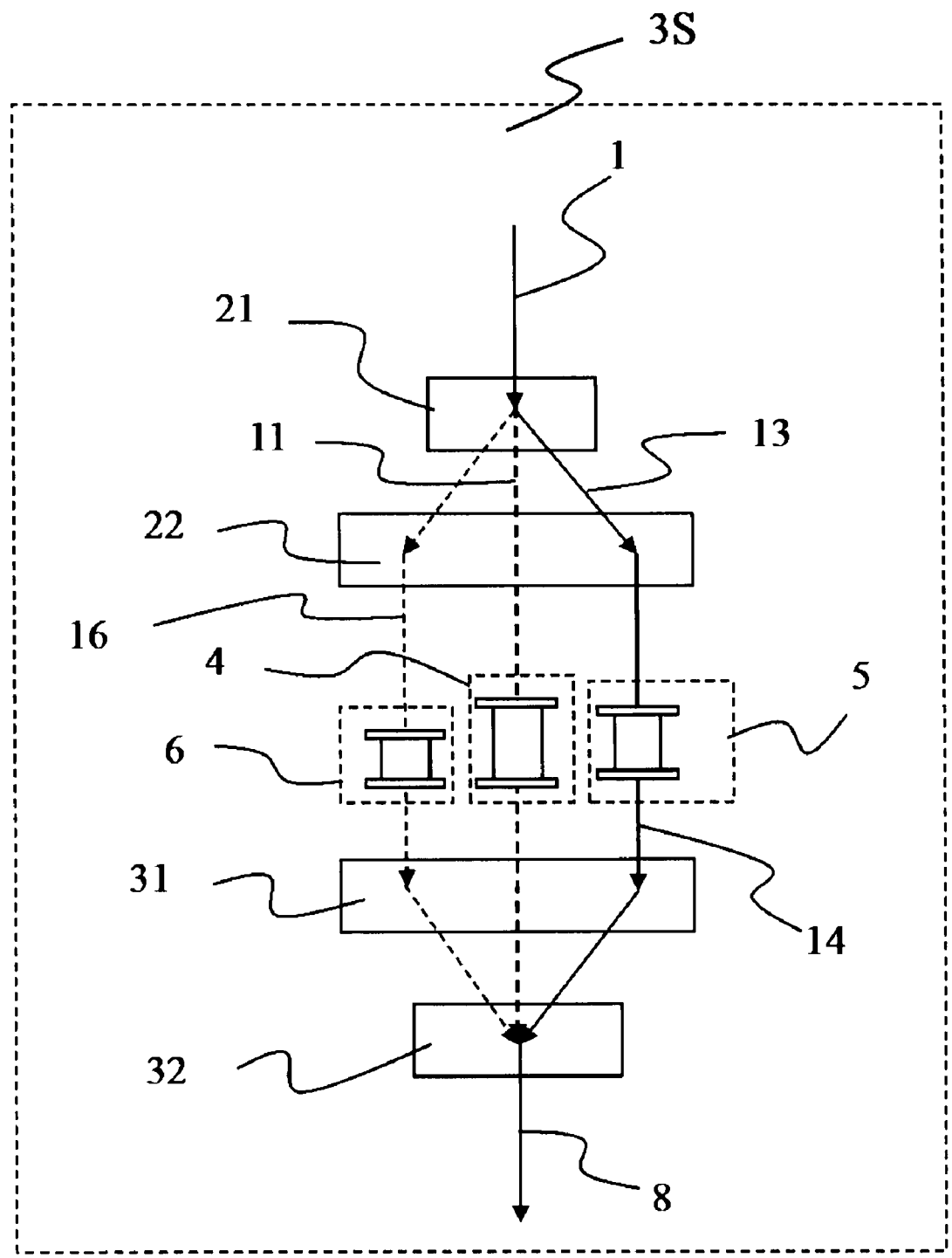
FIG. 7 is a schematic block diagram illustrating a beam energy changing unit according to Embodiment 4 of the present invention.

FIG. 7 is a configuration diagram of a beam energy changing unit 3S according to Embodiment 4 of the present invention. In FIG. 7, the same reference numerals as those in FIG. 1 denote the same or equivalent elements. In Embodiments 1, 2, and 3, two intra-apparatus beam orbits are provided; however, in Embodiment 4, a third intra-apparatus beam orbit 16 is also provided, i.e., three intra-apparatus beam orbits are provided. Because of the addition of the third intra-apparatus beam orbit 16, a third variable energy attenuation unit 6 is added.

In Embodiment 4, because three variable energy attenuation units are provided, the respective thicknesses of the three variable energy attenuation units can be made to correspond to the energies of beams to be irradiated in the next time and in the time after the next, while sequentially utilizing the three variable energy attenuation units during irradiation. Accordingly, it is only necessary for each variable energy attenuation unit to finish its changing operation in an irradiation time corresponding to two slices. Therefore, compared with Embodiment 1 or the like, the beam energy changing unit can meet the requirement of a further shorter slice irradiation time. Alternatively, in the case of the same slice irradiation time, compared with a beam energy changing unit utilizing two variable energy attenuation units, the operating speed of the variable energy attenuation unit may be decreased; thus, the noise and the mechanical vibration can be reduced.

The number of intra-apparatus beam orbits may be four; it goes without saying that the effect of the present invention is demonstrated, as long as the number of intra-apparatus beam orbits is two or more, i.e., a plurality.

Embodiment 5

Figure 8:
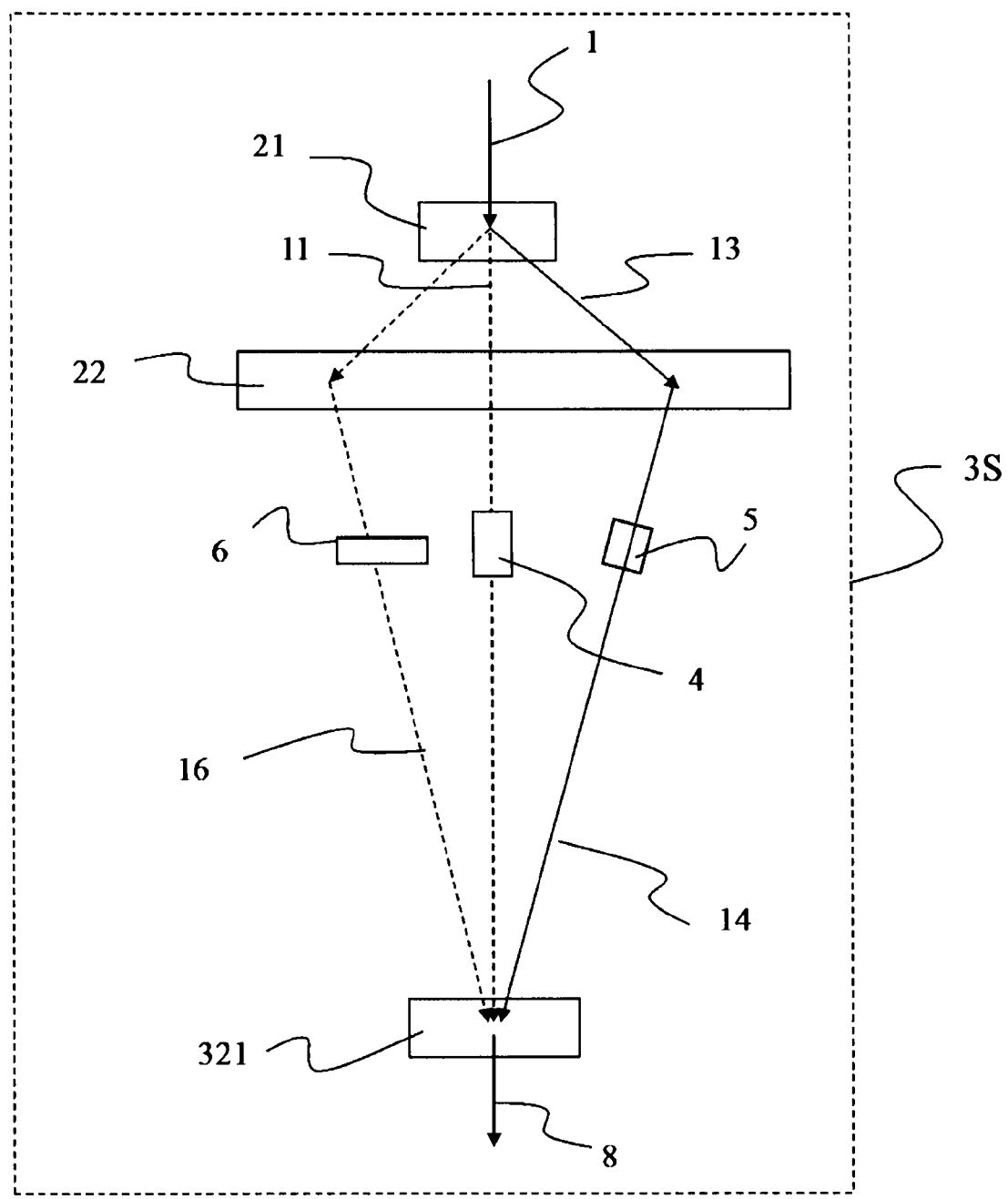
FIG. 8 is a schematic block diagram illustrating a beam energy changing unit according to Embodiment 5 of the present invention.

FIG. 8 is a configuration diagram of a beam energy changing unit 3S according to Embodiment 5 of the present invention. In FIG. 8, the same reference numerals as those in FIG. 1 denote the same or equivalent elements. In each of Embodiments 1 through 4, two sets, i.e., totally four deflection electromagnets are utilized; however, in Embodiment 5, three electromagnets are utilizes. Although two deflection electromagnets, i.e., the deflection electromagnets 21 and 22 are utilized for beam deflection at the incident side; however, only a single, i.e., the deflection electromagnet 321 is utilized for beam deflection at the exit side. Because of the above configuration, the three intra-apparatus beam orbits have no portions that are in parallel with one another.

In Embodiment 5, three, as the number of deflection electromagnets, is sufficient; therefore, the number of power sourced can be decreased. Accordingly, compared with each of Embodiments 1 through 4, the configuration of the apparatus can be simplified. In some particle beam therapies, there exists a case where one or two deflection electromagnets among three deflection electromagnets in FIG. 8 can be replaced with deflection electromagnets already existing in the particle beam transport unit or the irradiation unit. In other words, there exists an effect that the beam energy changing unit 3S according to the present invention can be built by use of a deflection electromagnet in the existing beam line. Accordingly, there exists an effect that the downsizing and the cost reduction of the apparatus can be realized.

Embodiment 6

Figure 9:
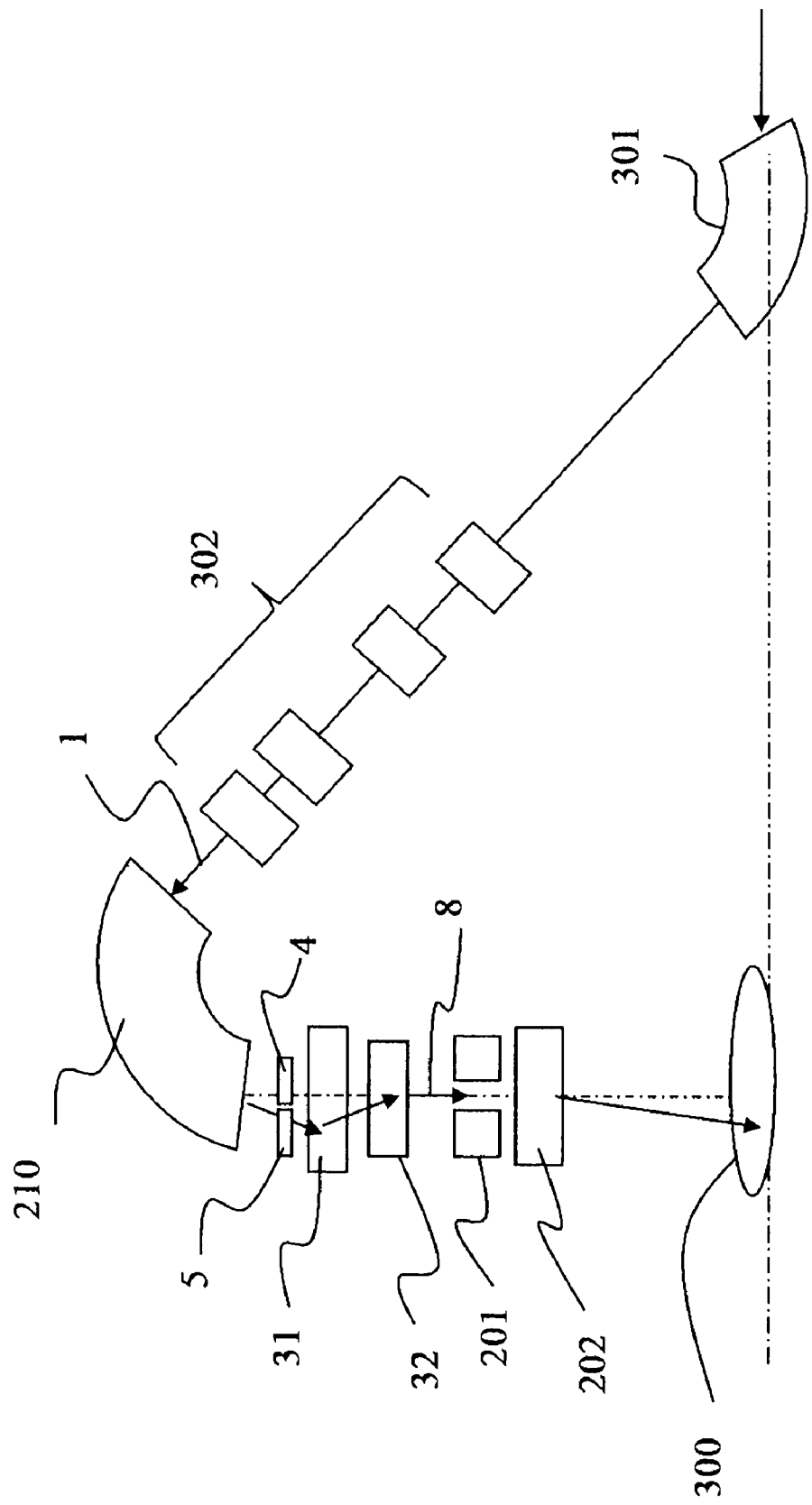
FIG. 9 is a schematic block diagram illustrating a beam energy changing unit according to Embodiment 6 of the present invention.

FIG. 9 is a configuration diagram of a beam energy changing unit 3S according to Embodiment 6 of the present invention. Embodiment 6 is an embodiment in which the present invention is applied to a vertical beam irradiation line, which can perform irradiation onto a patient from directly above, and a rotating gantry irradiation apparatus, which can rotate 360° so as to irradiate a beam onto a patient in a plurality of directions; the vertical beam irradiation line and the rotating gantry irradiation apparatus are utilized in a particle beam therapy system. In FIG. 9, the same reference numerals as those in FIG. 1 denote the same or equivalent elements. Reference numeral 301 denotes an added deflection electromagnet. Reference numeral 302 denotes beam transport electromagnets including beam converging electromagnets and deflection electromagnets. Reference numeral 210 denotes a deflection electromagnet that plays the role of a deflection electromagnet for bending a beam and the role of the first deflection electromagnet for forming two intra-apparatus beam orbits. Reference numerals 31 and 32 are the same as the third deflection electromagnet 31 and the fourth deflection electromagnet 32, respectively, in FIG. 1 or the like; they are deflection electromagnets for returning a beam to the orbit of the particle beam 8 whose energy has been changed.

The beam energy change control unit 4S makes each of the deflection electromagnet 210, the third deflection electromagnet 31, and the fourth deflection electromagnet 32 move between two excitation states; the incident particle beam 1 is made to travel through two different intra-apparatus beam orbits and finally becomes the energy-changed particle beam 8 that has passed through the variable energy attenuation unit 4 or 5. The energy-changed particle beam 8 is irradiated onto an irradiation subject 300 by means of 201 and 202.

By utilizing the particle beam therapy system according to Embodiment 6, the beam energy changing unit for rapidly changing beam energy can be provided in the small-space vertical irradiation beam line or in the nozzle of the rotating irradiation apparatus. Moreover, the variable energy attenuation units 4 and 5 can be provided relatively close to an irradiation subject; therefore, there can be reduced an effect, on the irradiation subject, that is caused because the size of a particle beam that passes through the variable energy attenuation unit 4 or 5 is increased due to angular variance. Accordingly, there is demonstrated an effect that a high-accuracy particle beam therapy system can be obtained.

Embodiment 7

Figure 10:
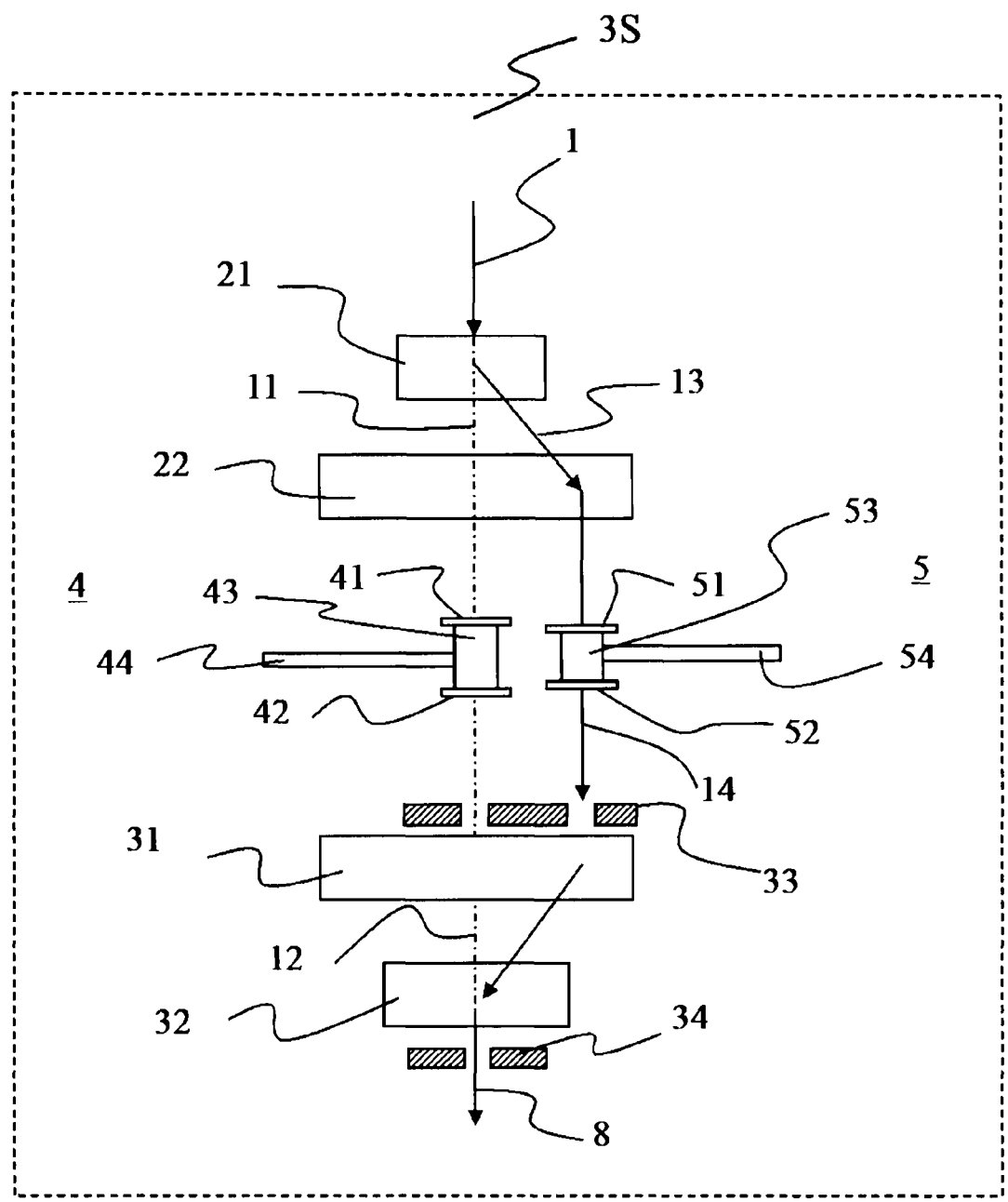
FIG. 10 is a schematic block diagram illustrating a beam energy changing unit according to Embodiment 7 of the present invention.

FIG. 10 is a configuration diagram of a beam energy changing unit 3S according to Embodiment 7 of the present invention. In FIG. 10, the same reference numerals as those in FIG. 1 denote the same or equivalent elements. In Embodiment 7, in order to limit the size of a particle beam in line with the first and the second intra-apparatus beam orbits, a collimator member 33 having an opening of a predetermined size is added before the third deflection electromagnet 31, and after the fourth deflection electromagnet 32, there is added a collimator member 34 having an opening of a predetermined size in order to limit the size of a particle beam. The shape of the opening is normally circular.

The operation of a particle beam therapy system according to Embodiment 7 is approximately the same as that of the particle beam therapy system according to Embodiment 1. In this regard, however, because of the addition of the collimator member 33, there is demonstrated an effect that there can be cut off the component, of a particle beam whose divergence angle has increased in some degree after passing through the variable energy attenuation unit 4 or 5, that is situated in the peripheral portion of the beam and has a large divergence angle. Accordingly, the energy of the particle beam transported to the irradiation unit can be changed while the small size thereof is maintained. Moreover, because of the addition of the collimator member 34, not only the energy-changed particle beam can be prevented from increasing its size, but also there can be cut off large-energy-dispersion portions, of the particle beam, most of which exist in the periphery. The energy dispersion, which increases because the particle beam has passed through the variable energy attenuation unit 4 or 5, can also be reduced. Therefore, because the beam size is suppressed from increasing until the particle beam 8 is irradiated onto an irradiation subject, there is demonstrated an effect that Embodiment 7 can contribute to downsizing of the electromagnet or the like in the irradiation unit.

In addition, in Embodiment 7, there has been explained a case where two collimator members, i.e., the collimator members 33 and 34 are provided; however, only one of the two collimator members may be provided. It goes without saying that the foregoing effect is demonstrated by providing a collimator member having an opening of a predetermined size at a position, between the variable energy attenuation unit and the irradiation unit, through which a particle beam passes.

Various modifications and alterations of this invention will be apparent to those skilled in the art without departing from the scope and spirit of this invention, and it should be understood that this is not limited to the illustrative embodiments set forth herein.

What is claimed is:

1. A particle beam therapy system comprising:
a beam energy changing unit that changes the energy of an incident particle beam;
a beam energy change control unit that outputs a command for controlling the beam energy changing unit;
an irradiation unit that irradiates a particle beam exiting from the beam energy changing unit onto an irradiation subject; and
an irradiation control unit that outputs a command for controlling the energy and position of a particle beam to be irradiated onto the irradiation subject,
wherein the beam energy changing unit includes deflection electromagnets that sequentially deflect the incident particle beam into a plurality of intra-apparatus beam orbits, a plurality of separate variable energy attenuation units disposed in the respective intra-apparatus beam orbits, and a deflection electromagnet that performs deflection in such a way that particle beams that pass through the respective variable energy attenuation units fall into a single and the same orbit; and while a particle beam passes through one of the variable energy attenuation units, the beam energy change control unit performs control in such a way as to change the energy attenuation amount of at least one of the other variable energy attenuation units, based on the command from the irradiation control unit, each variable energy attenuation unit configured to change the energy attenuation amount without changing energy attenuation amounts of other variable energy attenuation units or a path of the particle beam passing through the variable energy attenuation unit.

2. The particle beam therapy system according to claim 1, wherein the intra-apparatus beam orbits have portions that are in parallel with one another, and the variable energy attenuation units are provided in the respective parallel portions.

3. The particle beam therapy system according to claim 1, wherein the number of the intra-apparatus beam orbits is two.

4. The particle beam therapy system according to claim 1, wherein the number of the intra-apparatus beam orbits is three.

5. The particle beam therapy system according to claim 1, wherein the variable energy attenuation unit is configured in such a way as to be provided with a water introducing tube for introducing water into a shape-variable container whose side faces are formed of a shape-variable material, in such a manner that the pressure of water can be controlled, and in such a way that the thickness of a portion, of the shape-variable container, through which a particle beam passes can be changed by changing the pressure of water.

6. The particle beam therapy system according to claim 1, wherein the variable energy attenuation unit is configured in such a way as to be provided with a particle beam energy attenuator whose thickness changes in a single direction and as to be provided in such a manner that the single direction in which the thickness of the particle beam energy attenuator changes is slanted at a predetermined angle from a plane including a plurality of intra-apparatus beam orbits, and in such a way that an energy attenuation amount is changed by moving the particle beam energy attenuator in the single direction in which the thickness thereof changes.

7. The particle beam therapy system according to claim 6, wherein the predetermined angle is 90°.

8. The particle beam therapy system according to claim 1, wherein a collimator member having an opening of a predetermined size is provided at a position, between the variable energy attenuation unit and the irradiation unit, through which a particle beam passes.

* * * * *